United States Patent
Simas, Jr.

(10) Patent No.: US 8,641,680 B2
(45) Date of Patent: Feb. 4, 2014

(54) SAFETY NEEDLE DEVICE WITH SNAP FEATURE

(75) Inventor: Robert Simas, Jr., Keene, NH (US)

(73) Assignee: Smiths Medical ASD, Inc., Rockland, MA (US)

( * ) Notice: Subject to any disclaimer, the term of this patent is extended or adjusted under 35 U.S.C. 154(b) by 1920 days.

(21) Appl. No.: 11/029,371

(22) Filed: Jan. 6, 2005

(65) Prior Publication Data

US 2006/0149188 A1    Jul. 6, 2006

(51) Int. Cl.
   *A61M 5/32*    (2006.01)

(52) U.S. Cl.
   USPC .......................................... 604/198; 604/196

(58) Field of Classification Search
   USPC ............ 604/110, 198, 164.09, 192, 263, 196, 604/164.08
   See application file for complete search history.

(56) References Cited

U.S. PATENT DOCUMENTS

| | | | |
|---|---|---|---|
| 4,909,792 A * | 3/1990 | Norelli | 604/192 |
| 4,982,842 A | 1/1991 | Hollister | |
| 5,015,241 A * | 5/1991 | Feimer | 604/198 |
| 5,139,489 A | 8/1992 | Hollister | |
| 5,147,319 A * | 9/1992 | Ishikawa et al. | 604/174 |
| 5,154,285 A | 10/1992 | Hollister | |
| 5,232,454 A | 8/1993 | Hollister | |
| 5,232,455 A * | 8/1993 | Hollister | 604/192 |
| 5,277,311 A | 1/1994 | Hollister | |
| 5,423,765 A | 6/1995 | Hollister | |
| 5,662,617 A | 9/1997 | Odell et al. | |
| 5,891,103 A * | 4/1999 | Burns | 604/192 |
| 5,993,426 A | 11/1999 | Hollister | |
| 6,156,012 A * | 12/2000 | Nathan | 604/192 |
| RE37,110 E * | 3/2001 | Hollister | 206/365 |
| RE37,252 E | 7/2001 | Hollister | |
| 6,328,713 B1 | 12/2001 | Hollister | |
| 6,413,243 B1 * | 7/2002 | Geist | 604/192 |
| 7,112,190 B2 * | 9/2006 | Bressler et al. | 604/263 |
| 2002/0193744 A1 * | 12/2002 | Alesi et al. | 604/192 |
| 2005/0054986 A1 | 3/2005 | Simpson et al. | |

FOREIGN PATENT DOCUMENTS

| | | |
|---|---|---|
| JP | 6-304254 | 11/1994 |
| JP | 8-107933 | 4/1996 |
| JP | 2003-220139 | 8/2003 |
| JP | 2003-275308 | 9/2003 |

\* cited by examiner

*Primary Examiner* — Kevin C Sirmons
*Assistant Examiner* — Phillip Gray
(74) *Attorney, Agent, or Firm* — Louis Woo

(57) ABSTRACT

The present invention safety device is a one-piece needle assembly that has a base and a housing pivotally connected to the base. The base has a distal portion to which a needle is fitted. At the base there is formed longitudinally along its distal portion a catch mechanism that may be in the form of an anchor projection. At the back wall of the housing there is extended another catch mechanism that may be configured in the form of two clasping fingers. Also providing in the housing is an integral hook. As the housing and the base are pivoted relative to each other, and as the needle makes contact with the hook, the respective catch mechanisms at the base and the housing also make contact with each other, resulting in the coupling of the catch mechanisms and the coupling of the needle to the hook. As a result, the catch mechanisms are interlocked and the needle is fixedly retained by the hook within the housing. The catch mechanisms may also be configured as a hook and a latch in the form of a rib with an opening whereto the hook is fixedly coupled. The gauge of the needle may be determined by the color of both the base and the housing, which are molded as a unitary single unit.

17 Claims, 5 Drawing Sheets

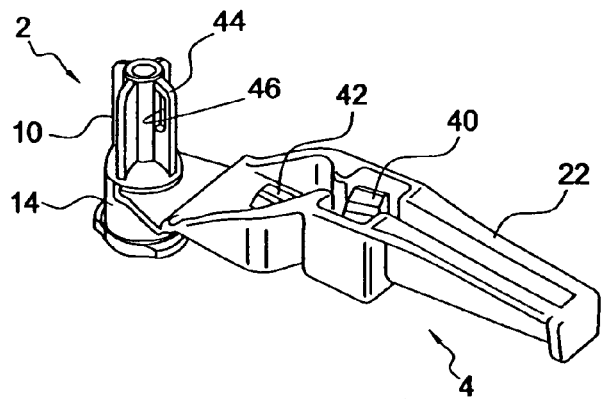
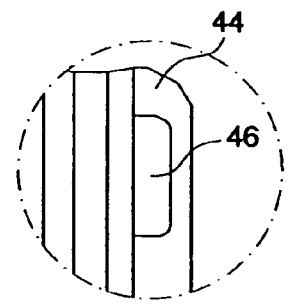
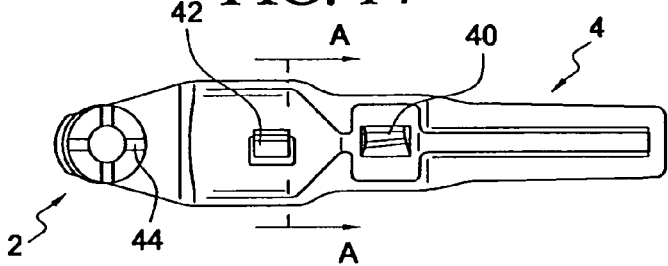
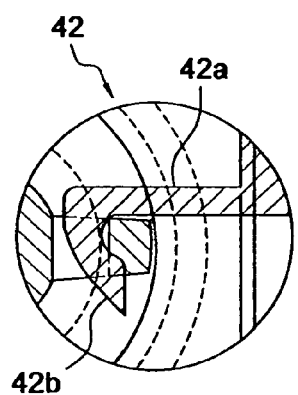
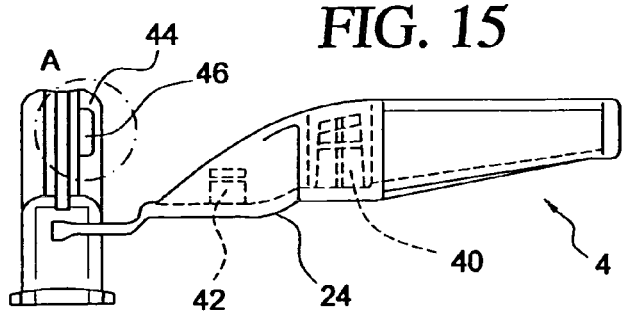
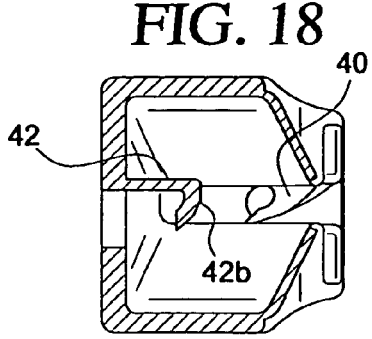
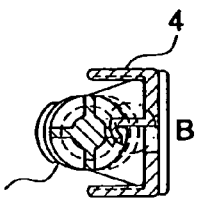

SAFETY NEEDLE DEVICE WITH SNAP FEATURE

FIELD OF THE INVENTION

The present invention relates to needle protection devices and more particularly to a needle assembly, adaptable to be used with a syringe, that includes mechanisms at the base and the housing of the needle assembly that coact to non-removably retain the housing and the base in a secured relationship, at the same time that the needle of the assembly is being fixedly secured by a hook mechanism in the housing.

BACKGROUND OF THE INVENTION

Needle protection devices that utilize a housing that pivots relative to the base are exemplified by a number of U.S. patents assigned to the assignee of the instant application. These include U.S. Pat. Nos. 4,982,842, 5,139,489, 5,154,285, 5,232,454, 5,232,455, 5,277,311 and 5,423,765, among others. There are other patents also assigned to the assignee of the instant invention that disclose the anchoring of the housing to the base of a needle. In U.S. Pat. RE37,110, RE37,252 and U.S. Pat. No. 6,328,713, there is disclosed the mating of an anchor at the base to an opening at the housing. Although feasible, it has been found that such embodiment entails the need for an anchor that has to be of a given length, as well as an opening that has to be well defined. Moreover, the portion of the housing where the opening is to be provided has to be sufficiently thin so as to provide the flexibility that enables the anchor to first pierce through and then be anchored to the opening. Further, with the anchor piercing through the housing, given that contaminated blood may well be splattered to the anchor as the housing closes over the contaminated needle, there may be a chance that contaminated fluid from the needle may be exposed on the backside of the housing where the anchor protrudes. Furthermore, such anchor based needle protection device is difficult to implement with a hook mechanism inside the housing, as the contact between the anchor and the opening at the housing would conflict with the retention of the needle by a hook in the housing, as exemplified by the aforenoted U.S. Pat. No. 4,982,842.

SUMMARY OF THE INVENTION

The present invention safety needle device has a locking mechanism that has one portion extending from the back wall of the housing and another portion extending from the base in such a way that when the housing is pivoted toward the base to cover the needle that extends from the base, the portions of the catch mechanism would couple together to fixedly retain the housing and the base relative to each other. One portion of the catch mechanism is configured to have two fingers closing in on a slot through which the other portion of the catch mechanism, in the form of an elongated anchor or projection, snaps into and be held by the fingers. The two portions of the catch mechanism are designed such that they would matingly couple at substantially the same time as the needle is clasped and be retained by an integral hook in the housing. This configuration ensures that a single pivoting movement of the housing relative to the base would enable the hook in the housing to fixedly retain the needle and at the same time enable the housing and the base be fixedly retained relative to each other. Two flaps each extending from a side wall of the housing prevent further access to the portions of the catch mechanism once those portions are coupled to each other. Each portion in turn may be considered a catch mechanism so that the safety device of the instant invention may be considered to have two coacting catch mechanisms.

The safety needle device of the instant invention is formed from the same mold such that the housing, the base, the portions of the catch mechanism as well as the hook, are integrally formed as a single unitary unit. The needle is fitted to the distal end of the base while the proximal end of the base is configured to be adaptable to a syringe or other medical apparatus for either withdrawing fluid from or ejecting medication to a patient. The needle that is attached to the base of the safety device of the instant invention may be of different gauges. To signify the gauge of the needle, the housing and the base of the safety device are color coded to a given color that has been predetermined to correspond to that given needle gauge.

The instant invention is therefore a needle assembly that has a base having a needle extending therefrom along a longitudinal axis thereof, a housing pivotally connected to the base with two side walls connected by a back wall, one portion of a catch or lock mechanism extends from the back wall so as to couple to another portion of the catch mechanism that extends from the base, so that once the portions of the catch mechanism are coupled to each other, the housing and the base are fixedly retained relative to each other, with the needle being covered by the housing.

The instant invention also relates to a one-piece needle assembly or safety device that is adaptable to be used with a syringe, with the respective portions of the catch mechanism being provided at the base and the housing per discussed above.

BRIEF DESCRIPTION OF THE FIGURES

The present invention will become apparent and the invention itself will be best understood with reference to the following description of the present invention taken in conjunction with the accompanying drawings, wherein:

FIG. 13 is a perspective view of the device of FIG. 11;

FIG. 14 is a plan view of the FIG. 13 safety device;

FIG. 15 is a side view of the FIG. 13 safety device;

FIG. 16 is an enlarged detail of the catch mechanism at the base of the safety device of FIG. 13;

FIG. 17 is an enlarged detail of the other catch mechanism of the safety device of FIG. 13;

FIG. 18 is a sectional view of the catch mechanism at the housing of the safety device of FIG. 13; and FIG. 19 is a cross-sectional view showing the interlocking of the catch mechanisms of the safety device of FIG. 13.

DETAILED DESCRIPTION OF THE INVENTION

Figure 1:
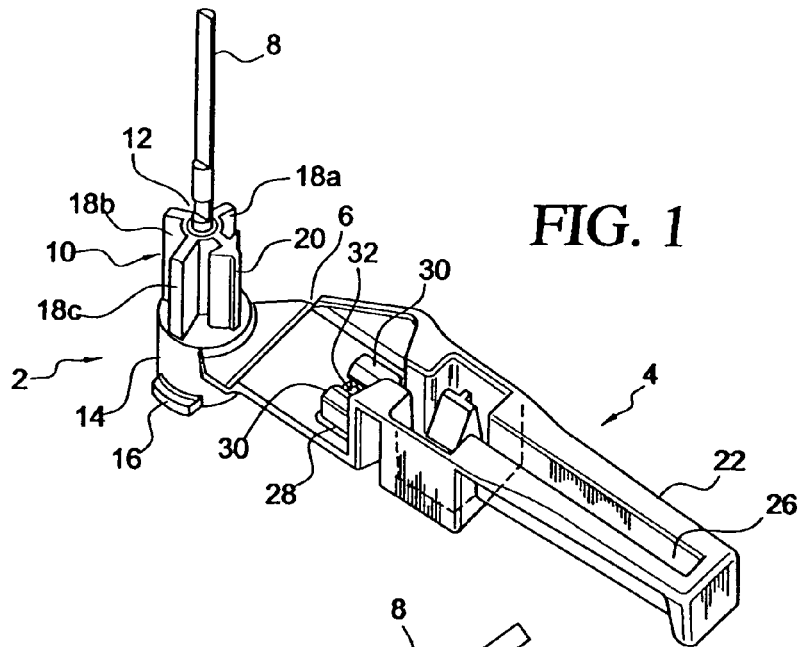
FIG. 1 is a perspective view of the safety device of the instant invention in a free standing position, with the housing being cross-sectioned.

With reference to the figures, the safety device of the instant invention is a needle assembly that has a base 2 and a housing 4 pivotally connected to the base by a living hinge 6. A needle 8 is adaptable to be fitted to the distal portion 10 of base 2. Needle 8 may be molded to the distal end 12 of base 2, or may be fitted thereto after the safety device has been removed from the mold. The proximal portion 14 of base 2 is configured to have a cavity that is adaptable to mate with a syringe, or other fluid storing devices, not shown. A luer connector 16 is provided at base 2.

There are a number of extensions 18a-18c provided at the distal portion 10 of base 2. There is moreover a catch mechanism 20 that extends from distal portion 10 of base 2 at a location facing housing 4. Catch mechanism 20 may be considered as one portion of an overall catch or locking mechanism, as explained below.

Figure 2:
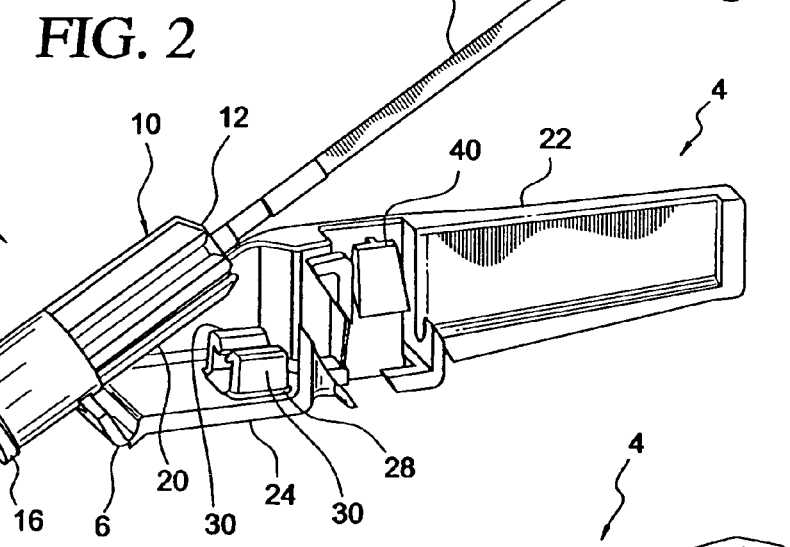
FIG. 2 is a view of the safety device of the instant invention, with the housing being shown in cross-section, as the housing and the base of the device are moved relatively towards each other.

Housing 4 is connected to base 2 via living hinge 6. Housing 4 has two sidewalls 22 connected by a back wall 24. A slot or passage 26 for housing 4 is defined by sidewalls 22. It is through passage 26 that needle 8 passes when housing 4 and base 2 are pivoted relative to each other, as shown in FIG. 2.

Figure 5:
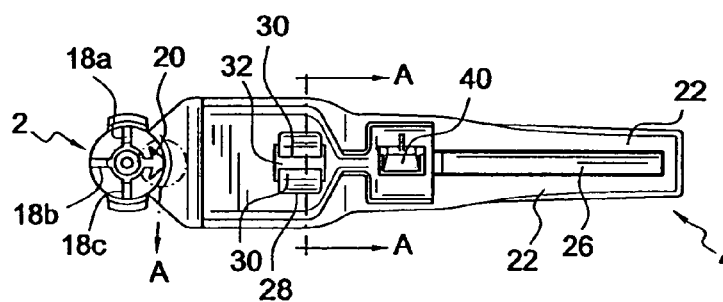
FIG. 5 is a top view of the safety device of FIG. 4.
Figure 6:
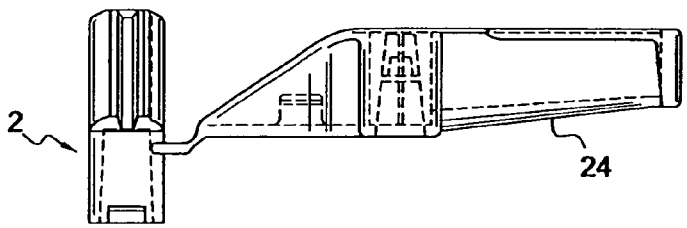
FIG. 6 is a side view of the safety device of FIG. 4.
Figure 7:
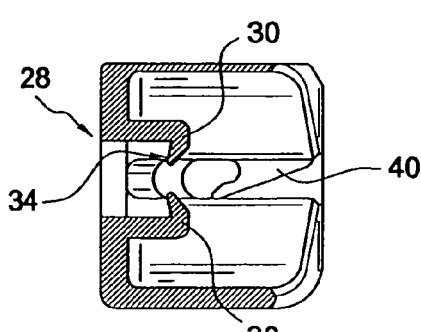
FIG. 7 shows the view at cross-section A-A of FIG. 5.

Extending from back wall 24 is a second catch or locking mechanism 28 that includes two grasping fingers 30. An opening 32 is configured between the grasping fingers 30. As best shown in FIG. 5 and the cross-sectional view in FIG. 7, each of the fingers 30 is configured to fold inward per its fingertip 34. The space defined by the fingers 30 is dimensioned to accommodate catch mechanism 20 at base 2 of the device, as best shown in FIG. 5 and the enlarged view thereof in FIG. 8.

Figure 3:
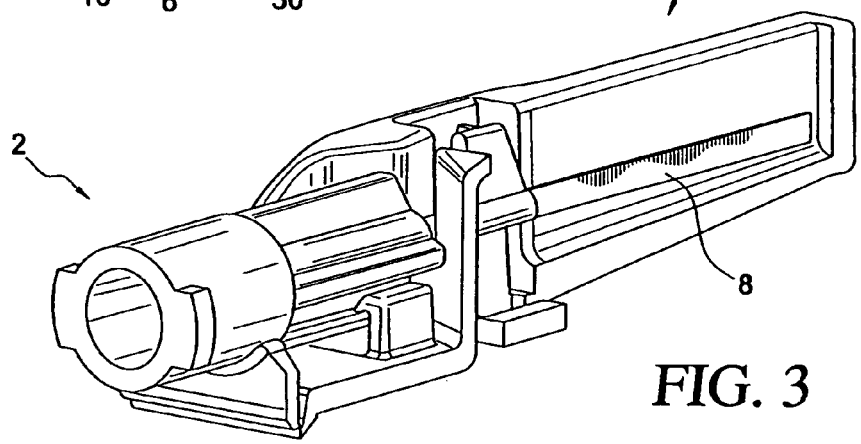
FIG. 3 shows the device in a fully actuated position with the locking snaps of the catch mechanism engaged.
Figure 4:
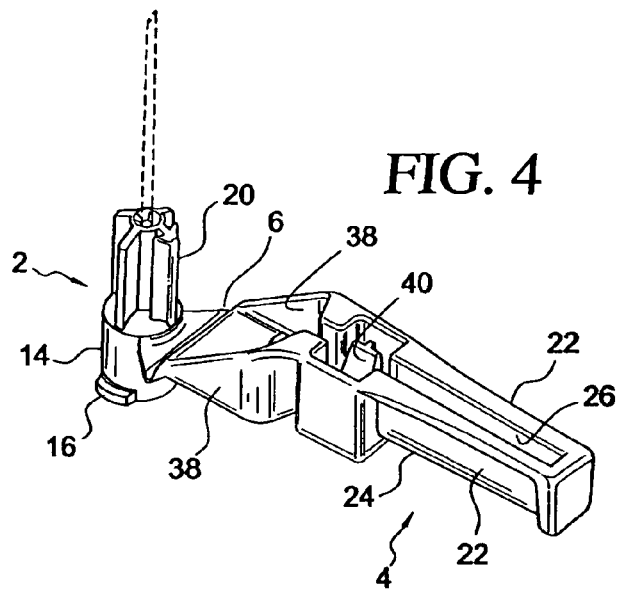
FIG. 4 is another perspective view of the device of the instant invention.
Figure 8:
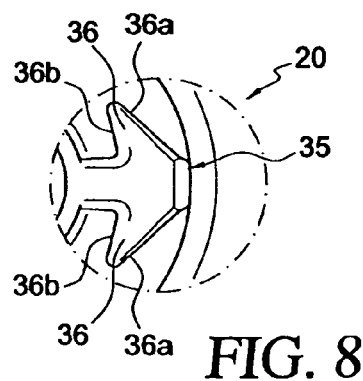
FIG. 8 is an enlarged view of detail A as shown in FIG. 5.

Catch mechanism 20 for the embodiment shown in FIG. 8 is in the form of an anchor or a projection that extends longitudinally along the distal portion 10 of base 2. Anchor 20 has a front surface 35 and two arrow shaped extensions 36. As the front surfaces 36A of the extensions 36 are inclined at an angle, when catch mechanism 20 meets with catch mechanism 28, the anchor extensions 36 would readily coact with the slant inward tips of fingers 30 to thereby readily engage with those fingers. The back surfaces 36b of catch mechanism 20 and the inwards folding finger tips 34 of catch mechanism 30 coact to prevent catch mechanism 20 and catch mechanism 30 from being removed from each other, thereby securely and non-removably coupling housing 4 to base 2. Thus, as best shown in FIGS. 2 and 3, when housing 4 and base 2 are pivoted relative to each other, as catch mechanism 20 at base 2 meets catch mechanism 28 at housing 4, catch mechanism 20 would snap into catch mechanism 30 so that both catch mechanisms interlock with each other, as best shown in FIG. 3. As discussed previously, catch mechanisms 20 and 28 may each be considered a portion of an overall catch or interlocking mechanism of the safety device of the instant invention.

Each of the sidewalls 22 has an extension 38 at its proximal portion. Together the side extensions 38 provide a protective environment for catch mechanism 28 that extends from the back wall 24 of housing 4. When catch mechanism 28 is interlocked with catch mechanism 20 as housing 4 is pivoted toward base 2 and covers needle 8, the side extensions 38 of housing 4 would prevent further access to the interlocked catch mechanisms to thereby impede any attempt to remove housing 4 from base 2.

Also integrated to housing 4 is a hook mechanism 40 that acts to clasp needle 8, when housing 4 is pivoted toward base 4 to cover needle 8. Hook 40 fixedly retains needle 8, once needle 8 snaps past the lip portion of hook 4 and is retained by the backside of the lip of hook 40.

As best shown in FIG. 2, the placement of hook mechanism 40 and catch mechanism 28, as well as the extension of those mechanisms from the back wall 24 of housing 4, are such that when housing 4 and base 2 are relatively pivoted toward each other, both needle 8 and catch mechanism 20 would make contact at substantially the same time with hook mechanism 40 and catch mechanism 28, respectively, so that both needle 8 and base 4 are secured to housing 4 at substantially the same time. By providing a combined interlocking of the needle and the base to the back wall of housing 4, needle 8 is ensured to be securely covered by housing 4 and not be re-exposed to the environment.

By providing catch mechanisms that extend from the back wall of the housing and from the base, and further configuring catch mechanism 20 to extend longitudinally along the distal portion of base 2, the coupling of housing 4 to base 2 is ensured to be more secured, as the coupling of housing 4 and base 2 is effected by the interlocking of the catch mechanisms as well as the clasping of needle 8 by hook 40. Thus, by effecting two catch points from the back wall of the housing, i.e., the interlocking of the catch mechanisms and the clasping of the needle by the hook, the housing is more securely held to the base to thereby ensure that the needle is securely covered. Further, by preventing access to the interlocked catch mechanisms, needle 8 could not be unlatched from hook 40.

Base 2 and housing 4, as well as the catch mechanisms 20 and 28 and hook 40, are formed as an integral unitary unit from the same mold. It may, for example, be injection molded.

Prior to use, needle 8 may be covered by a sheath, not shown, that fits over distal portion 10 of base 2. Further, the safety device of the instant invention may be molded or fitted with a number of different needles each having a different gauge. For the instant invention needle assembly, depending on the gauge of the needle fitted to the base, the safety device may be color coded to a predetermined color so that, without looking at needle 8 which is covered by the sheath, a user can readily ascertain the gauge of the needle. Thus, the molded one-piece unit of the safety device of the instant invention is color coded to have a predetermined color that signifies the gauge of the particular needle that is attached to its base. A more detailed discussion of such color coding of the needle to the body of the device is provided in application Ser. No. 10/751,982 having filing date of Jan. 7, 2004. The disclosure of the '982 application is incorporated by reference herein.

Figure 9:
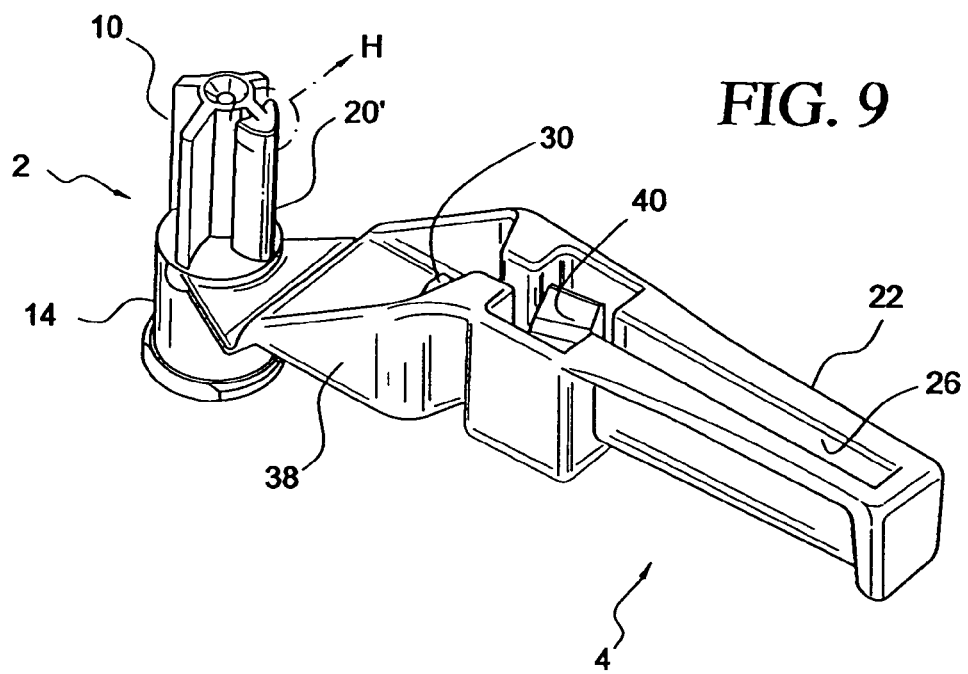
FIG. 9 is a perspective view of the instant invention safety device that has an alternative catch mechanism at the base of the device.
Figure 10:
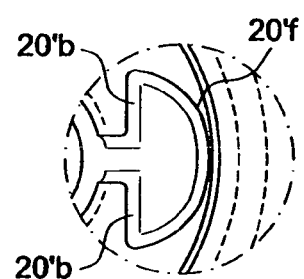
FIG. 10 is an enlarged detail of the alternative catch mechanism.
Figure 11:
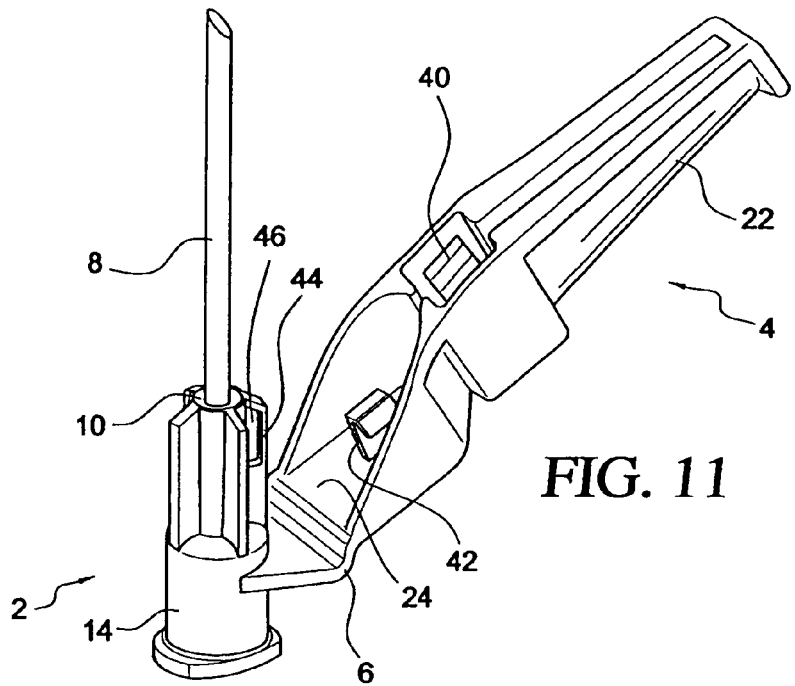
FIG. 11 is another embodiment of the instant invention safety device in which alternative catch mechanisms are provided at the base and the housing of the device.

An alternative embodiment of the catch mechanism at the base of the safety device is shown in FIGS. 9 and 10. The difference between the device shown in FIG. 9 and that shown in FIGS. 1-8 is the configuration of the anchor or projection 20'. As shown in greater detail in FIG. 10, catch mechanism 20' has a front surface 20'f that is curved, in contrast to the inclined side surfaces 36a of catch mechanism 20, as shown in FIG. 8. Furthermore, the back surfaces 20'b of projection 20' are not inwardly angled. The configuration of the tips of the respective fingers 30 could be adjusted to ensure that those fingertips could fixedly grasp onto the respective back surfaces 20'b, once the head of projection 20' is moved between the fingers and passed the fingertips. Like the previous embodiment, catch mechanisms 30 and 20' make contact substantially at the same time as hook 40 makes contact with the needle, not shown, that extends from the distal end 10 of base 2.

Figure 12:
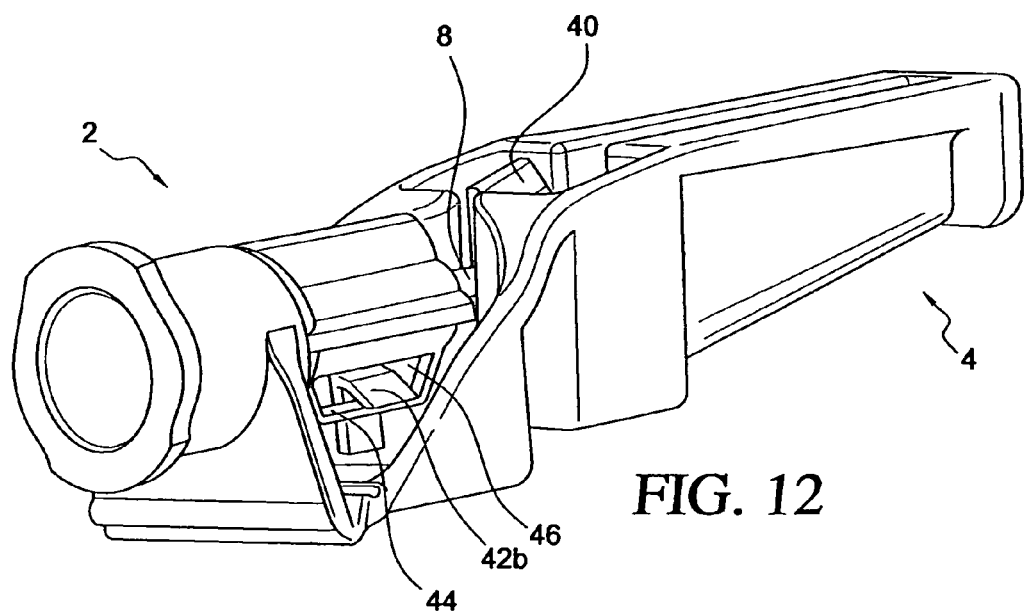
FIG. 12 illustrates the safety device of FIG. 11 in which the housing has been coupled to the base, with the catch mechanisms interlocked.

The catch mechanisms for the safety device shown in FIGS. 11-15 are different from those shown earlier. Specifically, the catch mechanism extending from the back wall 24 of housing 4 is configured in the form of a hook 42, as best shown by the enlarged detail illustration of FIG. 17. There it can be seen that hook 42 has an extension 42a and a tip 42b. Coacting with hook 42, at the distal portion 10 of base 2 of the safety device, is a latch in the form of a rib 44 that extends substantially longitudinally along the length of the distal portion 10 of base 2. An opening 46 is provided in rib 44. It is through opening 46 that the tip 42b of hook 42 latches onto, when housing 4 and base 2 are moved relatively toward each other. As best shown in the fully actuated position of FIG. 19, when hook 42 is interlocking with rib 44, housing 4 and base 2 of the safety device are fixedly retained relative to each other. FIG. 12 shows the fingertip 42b of hook 42 extending through opening 46 of rib 44, to thereby firmly latch onto rib 44. FIG. 12 also shows needle 8 being grasped by hook 40. Thus, a double hook safety device is effectuated by the embodiment of the safety device shown in FIGS. 11-15.

FIG. 14 is a plan view of housing 4, which is shown to have been pivoted away from base 2. In this view, both hooks 40 and 42 are clearly shown. The same is true with respect to the side view of the safety device shown in FIG. 15, where rib 44, and its opening 46, are clearly shown. The enlarged detail of the latch rib is shown in FIG. 16. The cross-sectional view A-A of the FIG. 13 safety device is shown in FIG. 18. As was noted previously, the fully activated safety device whereby the catch mechanisms at the housing and base are fully interlocked is shown in FIG. 19.

The invention claimed is:

1. A safety needle device, comprising:
a base having a body with a distal end wherefrom a needle extends, the body of the base and the needle extending along a longitudinal axis;
a housing pivotally connected to the base, the housing having two sidewalls connected by a back wall, the sidewalls defining a slot where through the needle passes when the base and the housing are pivoted relative towards each other so that the needle enters through the slot into the housing;
one catch mechanism extending from the back wall between the sidewalls of the housing to face the base when the housing and base are pivotally moved towards each other;
an other catch mechanism extending from the body of the base to face the housing when the base and housing are pivotally moved towards each other;
wherein the one catch mechanism and the other catch mechanism are configured to face each other and adapted to interlock with each other when the housing and base are moved to be in substantial alignment along the longitudinal axis; and
wherein when the base and needle are moved relatively towards each other with the needle passing through the slot and the housing in substantial alignment along the longitudinal axis, the needle is covered by the housing and the one and other catch mechanisms are interlocked with each other and housed within the housing so that access to the interlocked one and other catch mechanisms is prevented by the back wall and the sidewalls of the housing.

2. Device of claim 1, wherein the one catch mechanism comprises a pair of fingers and the other catch mechanism comprises a projection adapted to move between and be held by the fingers, the projection extending longitudinally along the longitudinal axis at a portion of the base.

3. Device of claim 1, wherein the one catch mechanism comprises a pair of catches and the other catch mechanism comprises two catches at an extension along the body of the base facing the housing, the catches of the one catch mechanism interlocking with the catches of the other catch mechanism when the one and other catch mechanisms are interlocked with each other.

4. Device of claim 1, further comprising a hook integrated to the housing for non-removably clasping the needle when the needle enters into the housing through the slot, the hook clasping the needle at substantially the same time that the one and other catch mechanisms interlock to each other.

5. Device of claim 1, wherein the base, the housing and the catch mechanisms are integrally formed as a single unitary piece usable with a syringe.

6. Device of claim 1, wherein the housing and the base are molded as a one piece unit that has a predetermined color that signifies the gauge of the needle.

7. Device of claim 1, wherein one of the catch mechanisms comprises one hook and the other of the catch mechanisms comprises a rib having an opening through which the hook latches to when the housing and the base are pivoted relatively towards each other.

8. A needle assembly adapted to be used with a syringe, comprising:
a base having a distal end;
a needle extending from the distal end of the base;
a housing pivotally connected to the base, the housing having two sidewalls connected by a back wall, the two sidewalls defining a slot for the housing where through the needle passes;
one catch mechanism positioned between the two sidewalls within the housing, the back wall and the sidewalls providing a protective environment for the one catch mechanism;
an other catch mechanism at an extension at the base that faces the housing when the housing and base are pivotally moved relative towards each other, the one and other catch mechanisms configured to interlock with each other; and
wherein when the base and needle are moved relatively towards each other with the needle passing through the slot and covered by the housing, the one and other catch mechanisms are fixedly interlocked with each other to prevent the housing and the base from being removed from each other, the interlocked one and other catch mechanisms positioned within the housing and prevented from being accessed by the back wall and the sidewalls of the housing.

9. Needle assembly of claim 8, wherein the one catch mechanism extends from the back wall of the housing between the two sidewalls.

10. Needle assembly of claim 8, wherein the one catch mechanism comprises a pair of first catches and the other catch mechanism comprises a projection at the extension with a pair of second catches, the first catches and the second catches correspondingly and non-removably engaged to each other when the one and other catch mechanisms are interlocked to each other.

11. Needle assembly of claim 8, further comprising a hook integrated within the housing to non-removably clasp the needle when the housing is moved to cover the needle and the one and other catch mechanisms are interlocking to each other.

12. Needle assembly of claim 8, wherein the base, the housing and the one and other catch mechanisms are integrally formed as a single unitary unit; and
wherein the single unitary unit is color coded to have a predetermined color that signifies the gauge of the needle.

13. Needle assembly of claim 8, wherein one of the one and other catch mechanisms comprises one hook and the other of the one and other catch mechanisms comprises a rib having an opening through which the hook latches to when the housing and the base are pivotally moved towards each other.

14. A safety device, comprising:
a base having a body with a distal end wherefrom a needle extends, the body of the base and the needle lying along a longitudinal axis;
a housing pivotally connected to the base, the housing having two sidewalls connected by a back wall, the sidewalls defining a slot where through the needle passes when the base and the housing are pivoted relative towards each other so that the needle enters through the slot into the housing;
one pair of catches extending from the back wall between the sidewalls of the housing so as to be positioned within the housing;
an other pair of catches formed at a rib extending from the body of the base orthogonal to the longitudinal axis to face the housing when the base and housing are pivotally moved towards each other;
wherein the one and other pairs of catches are configured to face each other and adapted to correspondingly interlock with each other when the housing and base are moved to be in substantial alignment along the longitudinal axis; and
wherein when the base and the housing are moved relatively towards each other with the needle passing into the housing through the slot and the housing in substantial alignment along the longitudinal axis, the respective catches of the one and other pairs of catches are correspondingly interlocked with each other so that the interlocked catches are positioned within the housing and prevented from being accessed from outside of the housing.

15. Safety device of claim 14, wherein the one pair of catches comprise a pair of fingers and the other pair of catches comprise two arrow shaped extensions adapted to be fixedly held by the fingers formed at the rib.

16. Safety device of claim 14, wherein the housing and base are molded as a single unit, and wherein the housing and base are color coded a predetermined color to signify the gauge of the needle.

17. Safety device of claim 14, further comprising a hook integrated within the housing to non-removably clasp the needle when the housing is moved to cover the needle, the hook clasping the needle at substantially the same time that the catches of the one and other pairs of catches interlocked to each other.

* * * * *